(12) United States Patent
Henkes et al.

(10) Patent No.: US 11,179,160 B2
(45) Date of Patent: Nov. 23, 2021

(54) IMPLANT HAVING A DETACHABLE MECHANISM

(71) Applicant: Phenox GmbH, Bochum (DE)

(72) Inventors: Hans Henkes, Stuttgart (DE); Hermann Monstadt, Bochum (DE); Ralf Hannes, Dortmund (DE)

(73) Assignee: Phenox GmbH, Bochum (DE)

( * ) Notice: Subject to any disclaimer, the term of this patent is extended or adjusted under 35 U.S.C. 154(b) by 37 days.

(21) Appl. No.: 16/311,327

(22) PCT Filed: Jun. 14, 2017

(86) PCT No.: PCT/EP2017/064530
§ 371 (c)(1),
(2) Date: Dec. 19, 2018

(87) PCT Pub. No.: WO2017/220400
PCT Pub. Date: Dec. 28, 2017

(65) Prior Publication Data
US 2019/0231358 A1    Aug. 1, 2019

(30) Foreign Application Priority Data

Jun. 23, 2016 (DE) .......................... 102016111568.1

(51) Int. Cl.
*A61B 17/12* (2006.01)
*A61B 17/00* (2006.01)
*A61B 90/00* (2016.01)

(52) U.S. Cl.
CPC .. *A61B 17/12113* (2013.01); *A61B 17/12172* (2013.01); *A61B 17/12177* (2013.01);
(Continued)

(58) Field of Classification Search
CPC .............. A61F 2/954; A61F 2002/9505; A61F 2002/9511; A61F 2/90; A61F 2/89;
(Continued)

(56) References Cited

U.S. PATENT DOCUMENTS

| 2003/0055440 A1 | 3/2003 | Jones et al. |
| 2012/0143317 A1* | 6/2012 | Cam ................ A61B 17/12172 623/1.35 |

(Continued)

FOREIGN PATENT DOCUMENTS

| WO | WO02106586 | * | 1/2002 | ............... A61F 2/06 |
| WO | WO2002000139 | | 1/2002 | |

(Continued)

OTHER PUBLICATIONS

International Search Report from IA No. PCT/EP2017/064530 dated Sep. 21, 2017.

*Primary Examiner* — Kathleen S Holwerda
*Assistant Examiner* — Uyen N Vo
(74) *Attorney, Agent, or Firm* — Crockett & Crockett, PC; K. David Crockett, Esq.

(57) ABSTRACT

An occlusive implant for bifurcation aneurysms (A), with the implant (1) being in an expanded state in which it is implanted in the blood vessel and in a contracted state in which it is movable through the blood vessel, with the implant (1) having a proximal fixing section (3) by means of which the implant (1) can be secured to the wall of a blood vessel, a distal section (5) where the implant (1) in expanded state is radially widened relative to the fixing section (3) and which is intended for placement in or in front of the aneurysm (A), and having a transition section (4) located between the fixing section (3) and the distal section (5), wherein fixing section (3) is attached to an delivery wire (2) in a detachable manner and wherein the transition section (4)

(Continued)

has a second detachment point (7) which enables the distal section (5) to be detached.

14 Claims, 5 Drawing Sheets

(52) U.S. Cl.
CPC ............... *A61B 2017/00526* (2013.01); *A61B 2017/00867* (2013.01); *A61B 2017/00929* (2013.01); *A61B 2017/00964* (2013.01); *A61B 2017/1205* (2013.01); *A61B 2017/12063* (2013.01); *A61B 2017/12068* (2013.01); *A61B 2090/037* (2016.02)

(58) Field of Classification Search
CPC ...... A61F 2/848; A61F 2/86; A61F 2002/823; A61B 2017/00867; A61B 2017/00929; A61B 2017/12127; A61B 2017/00964; A61B 2017/00969; A61B 2017/1205; A61B 2017/12054; A61B 2017/12063; A61B 2017/12077; A61B 2017/12081; A61B 2017/12086; A61B 2017/12068; A61B 5/02014; A61B 2090/037; A61B 17/12113; A61B 17/12172; A61B 17/12177
USPC .......................................... 606/119, 200, 202
See application file for complete search history.

(56) References Cited

U.S. PATENT DOCUMENTS

| 2012/0296362 | A1 | 11/2012 | Cam et al. | |
| 2013/0268046 | A1* | 10/2013 | Gerberding | A61B 17/12036 623/1.11 |
| 2014/0121752 | A1* | 5/2014 | Losordo | A61B 17/12118 623/1.12 |
| 2016/0051263 | A1* | 2/2016 | Morsi | A61B 17/12031 606/158 |

FOREIGN PATENT DOCUMENTS

| WO | WO2005070308 | 8/2005 |
| WO | WO2010028314 | 3/2010 |

\* cited by examiner

IMPLANT HAVING A DETACHABLE MECHANISM

FIELD OF THE INVENTIONS

The invention relates to an implant to be used for the occlusion of aneurysms in blood vessels in the region of vascular branches, in particular bifurcation aneurysms, with the implant being in an expanded state in which it is implanted in the blood vessel and in a contracted state in which it is movable through the blood vessel, with the implant having a proximal fixing section by means of which the implant can be secured to the wall of a blood vessel, a distal section where the implant in expanded state is radially widened relative to the fixing section and which is intended for placement in or in front of the aneurysm, and having a transition section located between the fixing section and the distal section, wherein the fixing section is attached to an introducer sheath in a detachable manner via a 1st detachment point and wherein the transition section having a 2nd detachment point which enables the distal section to be detached. Furthermore, the invention relates to a method for placing the implant in position.

BACKGROUND

Arteriovenous malformation may significantly impair a patient and may even result in fatal risks. This applies, in particular, to aneurysms, especially when these are found to exist in the cerebral region. Usually, it is attempted to occlude malformations of this nature by means of implants. In most cases, such implants are placed by endovascular methods using catheters.

Especially in the treatment of cerebral aneurysms, implanting platinum spirals has proven its worth, said spirals fill the aneurysm more or less completely, largely obstruct the blood inflow and enable a local thrombus or clot to form which fills and ultimately closes off the aneurysm. Nevertheless, this treatment approach is only suited for the treatment of aneurysms that have a relatively narrow access to the vessel system, so-called aciniform aneurysms. In the event of blood vessel protuberances having a wide access to the blood vessel there is a risk that the implanted spirals or coils may be flushed out. These can reach other areas of the vascular system where they may cause damage.

In such cases it has already been proposed to place into position a kind of stent that "bars" the opening of the aneurysm and in this way prevents the occlusion coils from being flushed out. Such stents are designed to have a relatively wide-mesh wall and are being employed in the treatment of some forms of aneurysms.

Vessel branches, in particular vessel bifurcations are a quite frequently occurring phenomenon. In the event of a weak vessel wall, the blood stream flowing through an artery and acting on the front wall in a bifurcation quickly causes a protuberance or bulge which is prone to rapidly dilate further. More often than not, such bifurcation aneurysms have a wide neck which prevents a therapy to be performed with occlusion coils only.

Vascular implants that are suitable to bring about such a "barring" of the aneurysm entrance in the area of a vascular branching have, for example, been disclosed in the international patent applications WO 2012/113554 A1 or WO 2014/029835 A1. The aneurysm can then be rendered non-hazardous as a result of occlusion coils inserted after the implant has been placed in position. It is also possible that the implant itself separates the aneurysm sufficiently from the blood flow. For this purpose, for example, the implant may have a membrane that is placed in the area of the aneurysm neck or in front of the aneurysm neck. If considered useful or expedient, the blood flow to the aneurysm can also be reduced with filaments alone, typically wires of small diameters, to such an extent that the additional introduction of occlusion coils or other occlusion means into the aneurysm can be dispensed with.

Implants known from the state of the art have a proximal section that is used to secure the implant in the vascular vessel and is essentially provided in the form of a conventional stent. A distal portion or section is provided at the distal end of the implant to be placed in or in front of the aneurysm which serves to cut off the aneurysm from the blood flow and/or prevent occlusion means introduced into the aneurysm from exiting the aneurysm and entering the blood vessel. An intermediate section may be provided between the proximal and distal sections that, for example, has a relatively low density of filaments to avoid or minimize the obstruction of the blood flow into the branching blood vessels.

The shaft-like proximal section, which serves to secure the implant in the carrier vessel, has proven to be valuable in many cases when placing the distal section in front of the aneurysm, in the area of the aneurysm neck or in the aneurysm itself. However, there are also cases in which an additional fixation of the distal section by a shaft-like fixing section is not necessary, since the distal section itself can already be anchored sufficiently well in the entrance area of the aneurysm. In such cases, the retention of the fixation section in the blood vessel system is actually unnecessary. As a general rule, one may proceed from the assumption that every additionally placed implant involves the risk that further complications may arise. In particular, depending on the vessel geometry, a too long fixing section can lead to complications during implantation.

Based on implants such as those described in WO 2014/029835 A1, it is thus the objective of the invention to provide a relevant implant that enables more variability in handling for the physician and, in particular, also allows placement of only the distal section in front of the aneurysm, in the neck of the aneurysm or within the aneurysm.

SUMMARY

According to the invention this objective is achieved by providing an implant to be used for the occlusion of aneurysms in blood vessels in the region of vascular branches, in particular bifurcation aneurysms, with the implant being in an expanded state in which it is implanted in the blood vessel and in a contracted state in which it is movable through the blood vessel, with the implant having a proximal fixing section by means of which the implant can be secured to the wall of a blood vessel, a distal section where the implant in expanded state is radially widened relative to the fixing section and which is intended for placement in or in front of the aneurysm, and having a transition section located between the fixing section and the distal section, wherein the fixing section is attached to an introducer sheath in a detachable manner via a 1st detachment point and wherein the transition section having a 2nd detachment point which enables the distal section to be detached.

The creation of a 2nd detachment point in the transition section between the fixing section and the distal section offers the attending physician additional possibilities. During the usual placement process of the implant they can choose to make a separation at the 1st detachment point, so that the shaft-like fixing section remains in the blood vessel system and in this manner secures the implant in its desired position. The distal section of the implant is placed in front of the aneurysm or within the aneurysm and held in place there by the fixing section.

If, however, the attending physician determines that the distal section alone is sufficiently fixed in the neck of or within or in front of the aneurysm and there is no danger that the distal section will be washed away by the blood stream, the physician may also decide to choose a detachment at the second detachment point. In this case, exclusively the distal section remains in the blood vessel system; the introducer sheath is retracted together with the fixing section and removed out of the blood vessel. It may also be advisable to exclusively leave the distal section in place if it is obvious that the placement of the elongated fixing section may give rise to difficulties, for example, due to excessive convolutions of the blood vessels or further branches situated proximal to the aneurysm.

The implant is preferably a self-expanding implant made of shape memory materials, so that the expansion and making contact with the inner wall of the vessel take place automatically by itself. Alternatively, the implant, in particular the stent-like fixing section, may also be expanded with the aid of a balloon onto which the fixing section is crimped, or by means of other mechanical techniques.

The fixing section has a stent-like tubular structure which may be produced by laser cutting, so that a surface is achieved that consists of webs between which openings exist. In addition, it is thought expedient to process the webs by electropolishing to make them smoother and rounder and thus render them less traumatic. This also reduces the risk that germs or other impurities may adhere to the webs.

As another alternative, the tubular structure may also consist of a wire braiding material, which forms a mesh structure. The wires in this case typically extend helically along the longitudinal axis, with intersecting opposed wires extending above and below each other at points of intersection resulting in honeycomb-like openings being created between the wires. The total number of wires preferably ranges between 3 and 64. As wires forming the mesh structure individual wires made of metal may be employed but it is also possible to provide strands, i.e. several wires of small diameter arranged so as to form a filament, preferably twisted around each other.

In the expanded state, the fixing section of the implant typically has a length of between 5 and 40 mm, preferably between 10 and 20 mm. The diameter in the expanded state is usually 1 to 10 mm, in particular 3 to 6 mm. Such a diameter is preferred for neurovascular applications. The length of the transition section of an expanded implant usually is in the range of between 1 and 15 mm, preferably between 5 and 12 mm.

The openings created in the tubular structure of the fixing section should be closed all around, that is, surrounded by webs or wires without interruptions (so-called "closed cell design"). In this way, the insertion of the fixing section into the microcatheter is facilitated by appropriately repositioning the catheter. This is important if the physician decides to carry out a detachment at the 2nd detachment point and remove the fixing section by pulling it back out of the blood vessel.

In that regard, the implant in general is to be viewed as a stent or stent-like object distinguished by its specialized way of application and design. The similarity to a stent applies in particular to the fixing section, while the distal section is widened radially outwards and may, for example, be provided with outwardly facing arches.

The wires or webs are especially made of metal. Particularly preferred is the use of shape memory metals such as nickel-titanium alloys, also known under the name nitinol. Ternary nickel-titanium alloys can also be put to use. It is also possible to make use of other alloys, polymers or other materials having shape memory properties or conventional stent materials such as medical steel or cobalt-chromium alloys. The use of materials having shape memory properties is advantageous in that it ensures that the implant automatically assumes its expanded shape upon liberation. Aside from using metal for the webs or wires these may also be made of a polymer material; in this respect, filaments made of a polymer material are also to be regarded as wires within the scope of the invention.

The webs/wires can have a round, oval, square or rectangular cross-section. Flat webs/wires in the form of thin strips, especially metal strips can be employed as well. In the case of a square or rectangular cross-section, it is advantageous to round off the edges.

Different detachment mechanisms can be selected for the 1st and 2nd detachment points. Mechanical, electrolytic or thermal detachment mechanisms are particularly suitable. Detachment mechanisms of this type are basically known in the state of the art.

A mechanical detachment mechanism is to be understood as a mechanism in which one section is connected by mechanical means to another section of the implant, in particular via a form-closed connection. However, it must be possible to exert influence on the connection from the outside with a view to detaching and liberating the distally located part of the implant. Connection elements may for example be provided on one section which interact with a suitably adapted retaining element of the adjacent section. One method in this context is that connecting elements and retaining elements are matched to each other in such a way that they interlock with each other in a form-closed manner and thus create a connection. However, the physician can take certain measures to ensure that the form closure separates resulting in the elements to be detached. For example, the connection elements and retaining elements may be surrounded by an enclosure that prevents the connecting elements from being detached from the retaining elements. However, if this enclosure is now removed, especially in the proximal direction, the connecting element can become unlocked and separate from the retaining element with the result that the relevant section of the implant is released. The interaction between connecting and retaining element can be similar to the lock-and-key principle. The enclosure may be, for example, a tube of plastic material, a sleeve of plastic or metal, a spiral helix of metal or may also consist of combinations thereof. If this detachment mechanism is provided for the 1st detachment point, it is possible to secure the enclosure to the introducer sheath by means of a clamping device to rule out unintentional displacement, for example with the aid of a torquer. In this case, the enclosure does not have to cover the entire introducer sheath; it is sufficient to extend the enclosure over the retaining element and the distal part of the introducer sheath.

To bring about the detachment it is also possible to make use of the microcatheter intended for the placement of the implant. In this case, the fixing section is detached from the introducer sheath at the 1st detachment point when the microcatheter is retracted in proximal direction beyond the 1st detachment point. However, care must be taken in this case to ensure that the microcatheter is only moved proximally beyond the 1st detachment point when it is certain that a detachment is really intended to take place at this position.

The connecting elements may, for example, have a spherical form, with the spheres being surrounded by corresponding recesses provided in the retaining element as long as no detachment has taken place. As soon as an external constraint that holds the connecting elements and retaining element together is removed, the spherical connecting elements move out of the recesses and detachment occurs. Following this, the portions of the implant located proximal to the detachment point can be withdrawn, in the case of the 1st detachment point the introducer sheath, in the case of the 2nd detachment point the introducer sheath and the fixing section. It goes without saying that the connecting elements do not have to be spherical, other types of geometric shapes, in particular thickenings/slubs, which can be gripped in a form-closed manner by a retaining element, are also suitable. It is not necessary to provide a single recess for each individual connecting element, instead a circumferential groove may be arranged for example that functions as a recess in which the connecting elements are held. It is also conceivable that the connecting elements are arranged at the more distally located section and the retaining element at the proximally adjacent section, as well as an inverse arrangement in which, for example, the connecting elements of the introducer sheath are embraced in a form-closed way by the retaining element at the fixing section.

The electrolytic detachment of implants is well known practice in the state of the art, for example for occlusion coils used for the purpose of closing off aneurysms. Relevant detachment points are described, for example, in WO 2011/147567 A1. The principle is based on the fact that when a voltage is applied, a suitably designed detachment point made of a suitable material, in particular metal, is dissolved as a rule by anodic oxidation at least to such an extent that the areas of the implant located distally to the corresponding detachment point are released. The detachment point can be made, for example, of stainless steel, magnesium, magnesium alloys or a cobalt-chromium alloy.

The dissolution of the detachment point is brought about by applying an electrical voltage. The electric power may be alternate current or direct current, with a low current intensity (<3 mA) being sufficient. The detachment point in this case usually functions as anode the metal of it being oxidized and dissolved.

The electrolytic severance is achieved by making use of a power source to apply an electric voltage to the desired detachment point. As already mentioned, this detachment point usually acts as anode whereas the cathode may be placed on the surface of the body, for example. It is to be understood that the detachment point must be connected in an electrically conductive manner with the power source, in particular via the introducer sheath. For this purpose, the introducer sheath itself must also be of electrically conductive design. Due to the fact that the corrosion-inducing current is influenced by the surface of the cathode, said cathode surface should be significantly greater than the surface of the anode. To a certain extent the speed at which the detachment point is dissolved can be controlled by appropriately sizing the cathode surface in relation to the anode surface. Accordingly, the invention also relates to a device comprising a power source and, where applicable or appropriate, an electrode to be placed onto the body surface.

It is also possible not to position the second electrode on the body surface, but to place both poles directly on the implant, which further accelerates the dissolution of the detachment point.

An electrolytic detachment point typically has a length ranging between 0.05 and 0.5 mm, in particular is approx. 0.2 mm long, and has a diameter of between 0.04 and 0.5 mm, in particular of approx. 0.1 mm.

In order to achieve a sufficient concentration of the current at a detachment point, it is viewed to be expedient to apply an electrically insulating coating to adjacent areas. If, for example, the 2nd detachment point is designed to be electrolytically detachable, it is advisable to apply an electrically insulating coating in whole or in part to the implant proximal to the 2nd detachment point. In particular, it is recommendable to arrange for an insulation between the 1st detachment point and the 2nd detachment point. Parylene, for example, can be used as a coating.

It is also possible to provide detachment points where the detachment method is combined by electrolytic and mechanical means. A mechanical connection, in particular brought about by a form closure, is established between the connecting elements and the retaining element, and this connection is maintained until an element that keeps up the mechanical connection is electrolytically corroded. According to a variant, thickenings/slubs are arranged at one section of the implant which via form closure are held in place by the retaining element, wherein a portion of the retaining element is designed so as to be electrolytically corrodible so that detachment is brought about when said portion has been dissolved electrolytically. For example, the detachment of the implant at the 1st detachment point can be effected by the electrolytic corrosion of a portion of the retaining element on the introducer sheath. The corrodible portion in this case is arranged such that it prevents the thickenings projecting into the retaining element from exiting. For example, this could be a pin that is arranged between the thickenings and keeps them apart so that they cannot detach from the retaining element. The fixation of the implant at the retaining element on the introducer sheath via form closure controlled by a portion of the retaining element being designed so as to be electrolytically separable, offers advantages in terms of accurate placement and also, as the case may be, repositioning or retraction of the implant.

Yet another possibility involves the corrodibly designed portion of the retaining element to be provided in the form of a disk having an opening, wherein the thickenings/slubs of the connecting elements extend through said opening and wherein the diameter of the opening is adapted to the thickenings in such a manner that said thickenings cannot pass through the opening as long as the disk is left intact. Only after the disk has been dissolved at least partially by applying a voltage will the thickenings of the implant be capable of exiting from the retaining element.

Another option is to design the detachment points as thermal detachment points. With a thermal detachment point, the connection between longitudinally adjacent sections of the implant can be broken by heating the detachment point, causing it to soften or melt so that a detachment is effected.

Expediently, different detachment mechanisms are selected for the 1st and 2nd detachment point. In this way, it is ensured that, depending on relevant requirements, different measures can purposefully be taken in dealing with the desired detachment point. For example, the following combinations are possible:

| 1st Detachment Point | 2nd Detachment Point |
| --- | --- |
| mechanical | electrolytic |
| electrolytic | mechanical |
| mechanical | thermal |
| thermal | mechanical |
| electrolytic | thermal |
| thermal | electrolytic |

A combination is preferred in which the 1st detachment point is designed to be mechanically detachable, with the 2nd detachment point being electrolytically detachable.

Preferably, originating from the fixing section the implant, when viewed in the longitudinal direction, converges closely in the transition section and then widens again in the distal section. The cross section of the implant in the longitudinal direction is thus considerably smaller in the transition section than in the distal section or in the fixing section. In the transition section, only one or several webs or wires are arranged close to each other, which increases the flexibility of the implant. High flexibility is desirable because many aneurysms do not have a regular shape but tilt to one side, for example. A flexible transition section can help ensure that the distal section adapts optimally to the shape of the aneurysm.

The webs/wires in the transition section may run at least to some extent through a sleeve which holds the webs/wires together in the transition section. In this context, "to some extent" means that the webs/wires in the transition section need not necessarily pass through the sleeve over their entire length; it is sufficient for part of the length of the webs/wires in the transition section to be embraced by the sleeve. In other words, the sleeve can be shorter than the transition section and the webs/wires that form the transition section.

Due to the fact that the webs/wires are held together in the transition section by a sleeve, they remain movable relative to each other to a certain extent but nevertheless are prevented from expanding radially beyond the intended extent. This also prevents one or several webs/wires from spreading radially in the transition section. Nevertheless, the implant is very flexible in the transitional section area and for that reason is capable of adapting well to the configuration of the blood vessels and the aneurysm. This is particularly important for the treatment of strongly asymmetric aneurysms and aneurysms that tilt to one side.

A thin design of the transition section also ensures that the flow of blood to branching off vessels is not or hardly impaired. In other words, the fixing section results in securing the implant in the carrier vessel when necessary, the transition section provides for sufficient flexibility as well as an unimpeded blood flow to and from vessels that branch off, and the distal section provides for the occlusion of the aneurysm, whereby the distal section can either directly minimize the flow of blood into the aneurysm or ensure that the occlusion means introduced into the aneurysm remain in the aneurysm.

Depending on the shape of the aneurysm and the shape of the implant, the distal section can be placed in the aneurysm itself or in front of the aneurysm, i.e. in front of the aneurysm neck on the side of the carrier vessel. In this context, placement in the aneurysm is also considered to embrace a placement in the neck of the aneurysm, said neck forming part of the respective aneurysm. As a rule, the distal section is positioned in the entry area of the aneurysm.

The term "sleeve" is to be understood broadly, that is, it may be provided in the form of a short tube, but other shapes or configurations may be used as well, provided that the sleeve has an inner cavity through which the webs/wires can pass. For example, the sleeve can be provided in the form of a collar. In particular, the sleeve can also be a wire coil that has an inner cavity.

It is important that, upon contraction of the implant, the sleeve does not slip or be displaced into the area of the fixing section or the distal section. In this case it may otherwise happen that the sleeve hinders the expansion of the implant after it has been liberated. Provided that the dimensions of the individual sections of the implant do not exclude the possibility of the implant slipping, it may make sense and be advisable to arrange for stoppers proximal and/or distal to the sleeve, said stoppers to prevent the sleeve from slipping or being displaced beyond the location of the stoppers. Said stoppers may be provided, for example, in the form of radial extensions in the transition section.

Another way to prevent the sleeve from slipping is to provide one or several webs/wires in the transition section with an eyelet, with the sleeve, in any case sections of it, extending through the eyelet, so that the sleeve is restricted in its mobility in the longitudinal direction of the implant. The eyelet can be created, for example, by one or several of the webs/wires having a larger cross-section in the transition section and by an opening existing in the web/wire in the area of the larger cross-section. Typically, the opening has an oblong form, so that a certain amount of longitudinal movement of the sleeve is allowed to ensure sufficient flexibility, but the longitudinal movement is limited by the distal and proximal ends of the eyelet. Normally, the opening is substantially orthogonal to the longitudinal axis of the implant. As a rule, the eyelet in the respective web or wire is located on the outer side so that the web/wire is otherwise surrounded by the sleeve, and with the sleeve moving through the eyelet. However, the reverse case is also conceivable, in which the eyelet points from the respective web/wire towards the center of the transition section; in this case as well, the sleeve extends through the eyelet, but the rest of the web/wire is situated outside the sleeve.

It is particularly advantageous if the sleeve is at least partially made of a radiopaque material. This, typically together with other radiopaque markers on the implant, enables visualization to be performed and thus control of the implantation process. In this context, the sleeve is preferably made of platinum, platinum alloys such as platinum-iridium or gold. It is possible to produce the sleeve, for example the wire spiral or coil, from the relevant material, but a coating, for instance, a gold coating is also conceivable.

In order to maintain a certain mobility of the webs/wires with respect to each other, it is preferred that the webs/wires run parallel to each other in the transition section. A slight twisting of the webs/wires is also conceivable, but this should not be too stiff in order not to endanger the adaptability of the implant.

As regards the placing process of the implant, the terms "proximal" and "distal" are to be understood such that they refer to parts of the implant that point towards the attending physician (proximal), or, as the case may be, to parts that point away from the attending physician (distal). Typically, the implant is thus moved forward in distal direction with the aid of a catheter. The term "axial" refers to the longitudinal axis of the implant extending from proximal to distal while the term "radial" denotes levels/planes extending vertically thereto.

At its proximal end the fixing section is connected to the introducer sheath via the 1st detachment point. Typically, the webs/wires of the fixing section converge in the direction of the 1st detachment point. The 1st detachment point is preferably situated at the periphery, that is, eccentrically arranged over the circumference of the fixing section in its expanded form, and when placement is done is in contact with the vessel wall when the implant has assumed its expanded form. It is also possible to allow the fixing section to converge proximally to form several, preferably 2 or 3 coupling elements, whereby these coupling elements preferably again lie in the radial edge area, eccentrically on the circumference of the fixing section. The coupling elements in turn are connected to the introducer sheath via the 1st detachment point. The provision of several coupling elements can improve the retractability of the implant, which is especially true when the fixing section is relatively short. In particular, the introducer sheath is a pusher wire. The eccentric arrangement of the 1st detachment point at the proximal end of the fixing section facilitates retraction of the implant into the placement catheter in the event of a misplacement. In addition, the flow of blood is less obstructed by an eccentrically arranged detachment point, especially if the fixing section remains permanently in the blood vessel. The introducer sheath is preferably made of stainless steel, nitinol or a cobalt-chromium alloy.

With the fixing section, the implant supports itself against the wall of the blood vessel in which the implant is implanted and is secured in this way. In this area, the vessel is undamaged and thus capable of supporting the fixing section which resembles a stent wall. In the event of self-expanding implants made of a shape memory material, especially a shape memory metal and preferably a nickel-titanium alloy, the fixing section is automatically brought into contact with the vessel wall when the implant has been liberated from the catheter whereas implants placed in position and dilated by means of balloons are pressed against the vessel wall in this area via a placement balloon. Self-expanding implants are preferred. However, if fixation by means of the fixing section turns out to unnecessary, detachment at the 2nd detachment point can also be performed and the fixing section is removed along with the introducer sheath after placement of the distal section.

In comparison to the fixing section and even more so to the transition section the distal section is in most cases radially enlarged outwardly. It serves to be placed into the aneurysm itself or in the area of access to the aneurysm, that is, at the aneurysm neck which it closes off, or it prevents occlusion means introduced into the aneurysm from exiting. Of primary importance is that blood coagulation ultimately takes place in the aneurysm. On the one hand, the surface coverage must be sufficiently large to either prevent any occlusion means introduced into the aneurysm from exiting the aneurysm or, due to an adequate amount of material, create a dense surface; on the other hand, a sufficient degree of flexibility of the implant must still be maintained to enable it to be introduced in the area of the bifurcation aneurysm.

In the expanded state, the distal section may have struts, loops or arches pointing radially outwards. These serve to anchor the implant in or in front of the aneurysm. Therefore, the shape of the implant in the distal section often resembles a blossom when viewed from the distal side. For example, the radially expanded distal section may have a radial diameter of between 2 and 20 mm, preferably between 5 and 15 mm. As a rule, there are at least two struts/loops/arches, in particular three struts/loops/arches or more. Typically, the number of struts/loops/arches ranges between 1 and 24, preferably between 2 and 8; said struts, loops or arches may be made from appropriately formed wire elements but in the event the implant is cut from a tube they may also be produced by adopting a laser cutting method to which said tube is then subjected, normally followed by a heat treatment. Said struts, loops or arches can be attached by adopting a laser welding method, for example. In the event loops or arches are provided, these preferably consist of wire elements originating from the transition section, then forming a bend and returning thereto, wherein said loops/arches may basically have optionally complex configurations. These may in particular also be three-dimensional objects depending on the shaping or configuration of the loops or arches. The loops or arches should be largely atraumatic and ensure that the sensitive vessel wall of the aneurysm remains unharmed. However, other filaments or struts may also be employed by means of which a radial expansion/enlargement of the distal section is achieved in comparison to the fixing section and the transition section. Said expansion may, for example, be of trumpet-, basket-like or blossom shape or provided in the form of a braiding. Outwardly protruding struts are preferably concentrically aligned radially inwards. At the same time the struts may protrude in distal direction. For example, two or more struts may each originate from a mutual connection point.

The angle the struts/loops/arches form in relation to the longitudinal axis of the implant after placement ranges between −45° and +175°, wherein a positive angle is indicative of struts/loops/arches pointing radially outward and a negative angle of struts/loops/arches pointing radially inward. In the event of relatively regular bifurcation aneurysms the angle preferably is in the range of between +45° and +90°; on the other hand, aneurysms are occasionally encountered that have an irregular shape, in particular a highly asymmetric shape. In such cases it may prove expedient to provide for significantly deviating angles of the struts/loops/arches. It may be useful, for instance, to provide for a very large angle in cases where the wall in one area of the aneurysm is strongly bulging out towards the blood supplying vessel. In such cases angles >90° are conceivable. In other cases, it may be helpful to provide for part of the struts/loops/arches to point inwards, that is, select negative angles to enable adaptation to the wall of the aneurysm. However, in case of implants having a very narrow transition section, the flexibility of the transition section alone means that the struts/loops/arches are capable of adapting well to the shape of the aneurysm even without having to preset particularly large or small angles. The angles may vary; in the event of an asymmetric aneurysm it may, for example, be helpful and expedient to provide for some loops to have angles >90° whereas other loops form customary angles ranging between 45° and 90°. It is of importance that said angles are formed after placement has been completed, i.e. relate to the expanded state; however, an implant in which the angles indicated here have not yet formed when in a condition prior to implant placement, e.g. due to external constraints, is also suitable according to the invention.

Angles that the struts/loops/arches form in relation to the longitudinal axis of the implant may, for example, range between 45° and 90°, −45° and 0°, 90° and 135° or 135° and 175°.

The struts/loops/arches in the distal section may be continuations of the webs/wires forming the remaining implant structure but may as well be separate filaments attached in the distal region of the remaining implant structure, that is, at the distal end of the transition section, for instance by means of a laser welding technique. In this context, each strut, each loop or each arch of the distal section may be connected to the remaining implant structure via one or a plurality of connection points, in particular only one or two connecting points per loop/strut/arch may be provided.

As an alternative to the design of the distal section comprising loops or arches, the distal section in expanded state may also be enlarged in spherical, mushroom-shaped, anchor-shaped or ellipsoid-shaped form. The forms mentioned above are to be viewed as alternatives which may also be employed to produce a radially expanded distal section. A spherical section, for example, can well adjust itself to the inner wall of the aneurysm because a regular bifurcation aneurysm often exists essentially in the form of a sphere. It is to be noted in this respect that within the scope of the invention a spherical form need not only be a true sphere as per its geometrical definition but may also have a deviating round, three-dimensional shape which is deemed to be a sphere within the meaning of the invention. In some cases, the form of the section is also comparable to an ellipsoid but it shall also be understood here that this need not be an exact spheroid in order to be regarded as ellipsoidal within the meaning of the invention. Moreover, sections may also have mushroom- or anchor-like shapes which are particularly suitable for the treatment of irregular aneurysms, for example if a wall portion of an aneurysm shows significant bulging in the direction of the supplying vessel. In the event of a mushroom or anchor form this is achieved in that some areas of the section extend in proximal direction. It shall be understood here as well that a section of mushroom- or anchor-like shape may also be asymmetric, for example may have areas that only on one side extend in proximal direction. The distal section may be made by laser cutting techniques or of braided design, with between 8 and 128 webs or wires being preferably used.

In the distal section, a central area may be provided with a view to obstructing the aneurysm, that is, to prevent the escape of occlusion means and/or separate the distal section from the flow of blood. The elements provided for this purpose are referred to as separation elements. On the one hand, the area may be designed to comprise introduced fibers, threads, thin wires, a membrane or similar separation elements but, on the other hand, may also be an integral part of the implant in the sense that the separation elements may be cut out of the basic tube and appropriately transformed or be composed of a wire braiding, for example in the shape of loops or strings. In the event of loops or strings these elements point radially inwards into the lumen of the implant, other than the above described loops of the distal section that at least for the most part point outwards. To make sure the inwardly arranged loops/strings do not interfere with each other it may be expedient to have them designed asymmetrically. The number may vary depending on the structure of the implant.

The threads making up the separation elements may be made of a polymer material, for example a polyamide such as nylon (polyhexamethylene adipic acid amide). It is also possible to use metal for this purpose, with shape memory alloys being preferred, in particular nickel titanium alloys such as nitinol.

Another possibility is to provide a membrane as separation element, said membrane being largely or completely impermeable to blood and in this way capable of separating the aneurysm from the blood flow. In the event the aneurysm can almost completely be isolated from the blood flow, an introduction of occlusion means into the aneurysm may, circumstances permitting, be dispensed with so that the separation element in this case does not serve to retain occlusion means. The membrane can be fixed to the struts/loops/arches and/or stretched on a braid of threads or wires, e.g. threads or wires can form a structure over or onto which the membrane is stretched. Additionally, further threads/wires are conceivable which, for example, may extend or be arranged to form a cross or crosshairs. Nevertheless, an arrangement of threads or wires is not necessarily needed for this purpose, the central area of the distal section may also be spanned over without the use of additional threads or wires.

The provision of a membrane as separation element is to be considered advantageous in that said membrane compactly folds together in distal or proximal direction when the implant is placed in the catheter so that an implant can be made available that in expanded condition has a largely impermeable separation element and when in contracted state is capable of also passing easily through narrow blood vessels. Otherwise, in comparison to an implant without separation element the structure of the implant described hereinbefore is largely the same.

However, even in cases where a membrane is provided as separation element it may still be of advantage to additionally introduce occlusion means into the aneurysm. For this reason, it may be expedient to use a membrane that has one or several cutouts so that occlusion means, in particular coils, can be placed into the aneurysm through these cutouts. Said cutout should be appropriately sized such that a catheter can be pushed through it into the area of the aneurysm, with the placement of the respective occlusion means being done via this catheter. On the other hand, the neck of the aneurysm should be covered to such an extent that the occlusion means are prevented from exiting the aneurysm in an uncontrolled manner, with any threads/wires spanning the area of the membrane in this case may perform an additional retaining function. It goes without saying in such a case that the threads or wires must not be spaced too closely so as not to interfere with a catheter passing through and introducing the occlusion means.

To enable occlusion means to be introduced into the aneurysm, the membrane may also be designed so as to be pierceable partially, with such a piercing effect being typically brought about by a microcatheter or guidewire. Through the opening so created a microcatheter is then passed by means of which the occlusion means are placed in position. The membrane should be designed in such a such way that after it has been pierced it remains partially intact to ensure it continues to prevent the occlusion means from exiting again. For example, threads or wires arranged as additional separation elements that may be arranged in the form of crosshairs can ensure that only a segment of the membrane forms an opening when being pierced whereas the other segments of the membrane remain covered due to the fact that the marginal areas of the membrane are stabilized and safeguarded by the threads/wires against rupturing. The membrane being provided as separation element may either be a single membrane which is to be pierced only partially or may consist of several smaller membranes.

Instead of or in addition to providing a membrane as separation element, it may be useful or expedient to arrange membranes in the interior of the (wire) loops or arches forming the distal section. Membranes may also be provided between struts of the distal section. Also, spherical, mushroom-, anchor- or ellipsoid-shaped distal sections can be covered with a membrane. When placed in front of or in the entry area of the aneurysm, the membranes can either be used to deflect the blood flow into branching vessels or prevent the flow of blood into the aneurysm.

The membrane need not be limited to the separation element and the interior of the loops/arches but may span the totality of distal section, so that the struts, loops or arches may serve to hold the membrane in place. For example, membranes may be arranged in the interspaces between the struts, loops or arches.

Even if the distal section is formed, wholly or in part, by filaments other than loops it is possible to arrange membranes in this location. For example, one or several membranes may be put up by means of struts protruding radially outwards. In such a case the structure resembles an umbrella, that is, when the distal section is expanding the unfolding struts put up between them one continuous or several membranes. By providing a plurality of struts and in this way a corresponding number of strut ends, a larger and more circular area can be covered by the membrane resulting in the interspaces to be reduced in size.

For the purpose of delimiting and reinforcing the membrane, threads may also be spanned between the individual struts/loops/arches, that is, the membranes are limited at least partially at the sides by one or several threads serving to connect the struts/loops/arches with each other. Such a delimiting of the relevant membrane must not necessarily take place via a thread in every direction, even the struts/loops/arches themselves may to some extent serve this purpose. For example, the outer edge of the membrane which is often situated further distally may be bordered by threads while the inner edge be formed by struts/loops/arches. In comparison to a membrane without delimitation at the sides an additional protection of the membrane is achieved in this way so that damage and cracks can be avoided. The threads are preferably made of a polyamide such as nylon.

The membrane (whether used as a separation element or located in other areas of the distal section) may be made of a polymeric material such as polytetrafluoroethylene, polyester, polyamides, polyurethanes or polyolefins. Especially preferred are polycarbonate urethanes. It is especially desirable to provide for an integral connection of the membrane with the threads or wires provided, where applicable, as additional separation elements. Such a connection may be achieved by coating the threads/wires by immersion or spraying techniques.

Preferably, the membrane is produced by an electrospinning process. By applying an electric current, fibrils or fibers are separated from a polymer solution and deposited on a substrate. Said deposition causes the fibrils to agglutinate into a non-woven fabric. As a rule, the fibrils have a diameter ranging between 100 and 3000 nm. Membranes created by electrospinning have a very uniform texture and may embrace a basic structure consisting of threads or wires. The membrane is tenacious, withstands mechanical stresses, and can be pierced mechanically without an opening so created giving rise to cracks propagating from it. The thickness of the fibrils as well as the degree of porosity can be controlled by selecting process parameters as appropriate. In the context of producing the membrane and with respect to materials suitable for this purpose, special attention is drawn to publications WO 2008/049386 A1, DE 28 06 030 A1 and literature referred to therein.

Also of advantage is an implant that uses as separation element a membrane which is in contact with the inner side of the implant, wherein said membrane in turn is permanently attached to further outer membrane sections filling out the individual loops or arches of the distal section. Such a membrane structure can be produced by electrospinning. In this case, the inner and outer membrane sections are partially connected; where the inner membrane section has no connection with the outer membrane section, it contracts similar to a nylon stocking, resulting in an opening for the introduction of occlusion means.

Instead of using an electrospinning method, the membrane may also be produced by an immersion process.

A membrane serving as separation element does not in every case (in the expanded state) have to lie in a plane orthogonal to the longitudinal axis of the implant, but in the expanded state as well may have an alignment in proximal direction. Although the membrane in its peripheral area is secured in this case to the circumference of the implant, the middle region of the membrane, however, extends in proximal direction. In this way, a conical or pyramid shape is formed wherein the base of the cone/pyramid is oriented orthogonally to the longitudinal axis, with the membrane in its peripheral region being attached to the implant whereas the apex of the cone/pyramid is situated further to proximal. In this manner, the flow of blood is divided and directed sideways when coming into contact with the membrane so that the ingress of blood into the aneurysm is largely prevented.

Even if the membrane provided as separation element has a conical or pyramid shape, said membrane may also be provided with one or a plurality of cutouts to make sure occlusion means may continue to be introduced into the aneurysm through said cutouts after the implant has been placed in position.

To make sure the conical or pyramid shape of the membrane can be maintained on a permanent basis, the membrane should be secured to a framework structure of threads or wires, but basically this structure may also consist of strings/lands cut, for instance by means of a laser, out of the structure forming the implant. Care must be taken in this case that the threads/wires are of adequate stiffness to prevent the membrane from undergoing reorientation or turning inwards as a result of the blood pressure. It may be necessary in this respect to introduce additional threads or wires.

Another possibility is to create crosshairs consisting of two relatively long individual threads to which the membrane is attached, with the membrane initially not being tensioned due to the length of the individual threads. Moreover, one or several threads may be attached to a further proximally situated loop of the implant so that the crosshairs and thus the membrane is spanned/tensioned in proximal direction as soon as the implant undergoes stretching. It shall be understood, however, that the crosshairs must not necessarily be composed of two threads only but other thread braidings of nearly unlimited configuration are conceivable as well that establish a type of framework impressing a structure onto the membrane.

Generally speaking, it is of importance for the invention that the distal section, possibly with the separation element, performs its intended function that is to reliably retain occlusion means, for example occlusion coils, introduced into the aneurysm or deflect the flow of blood in such a manner that further occlusion means are not needed. With the implant being expanded, the separation element also has at least one component arranged orthogonally to the longitudinal axis of the implant.

If the separation elements are formed by the insertion of fibers, threads or thin wires, it is advisable to arrange eyelets in the distal section to which the threads are secured by knotting following a cross- or star-shaped pattern. The eyelets proper can be made of fiber material. The threads/fibers consist, for example, of a suitable polymer such as a polyamide (nylon) or be composed of metallic fibers.

However, arches or (wire) loops cut from a tube material and bent into the implant body may also be used as separation elements. At least one arch/one loop is required for this purpose. If between two and four arches/loops are used, these will form a stable separation element which reliably retains the occlusion means introduced into an aneurysm.

When contracting the implant, the loops are typically stretching in proximal direction and thus lean against the other elements of the implant so that the implant may be easily moved through a catheter without causing problems. Slot-shaped openings can be left between the loops through which occlusion means can be inserted into the aneurysm. Alternatively, it is also possible, however, to provide the loops and/or the interspaces between the loops with a membrane to enable an impermeable as possible separation element to be achieved. Basically, membranes may also be used that are provided with one or several openings.

With regard to the various possibilities of designing the separation elements or providing the distal section with membranes, reference is also made to WO 2014/029835 A1, the content of which shall also be the subject of the disclosure of the present invention.

The distal section of the implant provided by the invention is designed so as to be particularly atraumatic, soft, and elastic. Walls of aneurysms are rather delicate and may rupture when forces are applied so this must be prevented. To this end, especially the distal section of the inventive implant should be designed so as to be atraumatic. This is achieved, for example, by an arrangement of loops or arches that adjust gently to the wall of the aneurysm in places where they are in contact. Same as other regions of the implant, such loops or arches may be produced by laser cutting from a tube, created by means of affixed wires or produced by a uniform wire braiding.

In the distal section, all wire ends should be made so as to be atraumatic to prevent perforation of the aneurysm wall.

As a rule, the implants according to the invention are provided with radiopaque marker elements facilitating visualization and their positioning at the placement site. For example, a sleeve provided in the transition section may be such a marker element. Moreover, marker elements can be arranged, for example, in the area of the distal end of the distal section and may shape the connection points of joined wires so as to be atraumatic. Such marker elements can also be provided in the form of wire windings, as collars and slotted tube sections that are secured to the implant. For example, marker coils surrounding the elements that are forming the loops can be provided as marker elements, whereby as a rule not the entire loops but, for example, only half of them are surrounded by marker coils. For said marker elements, in particular platinum and platinum alloy materials are suitable, for example alloys of platinum and iridium, as they are frequently used according to the state of the art for marking purposes and as material for occlusion coils. Other usable radiopaque metals are tantalum, gold, and tungsten. Ideally, the distal section and in particular the loops/struts/arches in the distal section are completely or in part designed so as to be radiopaque, i.e. they are made to be visible during radiography. It is also possible to coat or fill the webs/wires with radiopaque material.

It is also possible to make use of radiopaque substances in the membranes. These may be radiopaque particles as they are customarily employed as contrast medium for radiographical purposes. Such radiopaque substances are, for example, heavy metal salts such as barium sulfate or iodine compounds. A radiopaque membrane proves beneficial during placement of the implant and for localization purposes and may be used either additionally to or instead of marker elements. Another alternative is a partial gold coating of areas of the implant, such as the loops or certain areas of the loops.

If thought expedient, part of the implant may be formed using struts or wires of thinner cross section with a view to increasing the implant's flexibility. Preferably, the area is situated in the fixing section and intended to meet requirements associated with an irregular blood vessel configuration in the fixing zone.

The implant may be coated in a manner known per se. Suitable coating materials are, in particular, those described for stents, for example materials having antiproliferative, antiphlogistic, antithrombogeneous properties or hemocompatible characteristics conducive to ingrowth and/or preventing deposits.

The device proposed by the invention may, in particular, be used in the neurovascular field; it may, however, also be employed in the cardiovascular or peripheral region.

The invention also relates to a method for introducing the implant according to the invention into the blood vessel system. This can be brought about with the help of a customary microcatheter, which is a proven and frequently adopted technique. In case the neck of the aneurysm is not sufficiently sealed off already by the implant, occlusion means are introduced into the aneurysm after the implant has been placed in position. For this purpose, the distal end of a catheter is moved into the aneurysm following which the occlusion means, in particular coils, are introduced. To introduce the occlusion means, the catheter can be advanced through the implant, especially through the interior of the fixing section, into the aneurysm, whereby the fixing section provides a certain guidance of the catheter. When this has been done the catheter is retracted while the implant prevents the occlusion means from exiting the aneurysm. Aside from customary occlusion means such as coils, bodies of other shape and configuration may also be employed to close off aneurysms, for example spherical bodies of a braided design or formed differently. Irrespective of whether additional occlusion means are introduced into the aneurysm, severance takes finally place at the 1st or 2nd detachment point and the introducer sheath is withdrawn out of the blood vessel system with or without the fixing section, while the distal section and, should it be required, the fixing section remain in the blood vessel.

BRIEF DESCRIPTION OF THE DRAWINGS

Further elucidation of the invention is provided by way of example through the enclosed figures where

FIG. 1 shows a bifurcation aneurysm with a blood supplying vessel Z, two branching vessels X and Y and the aneurysm A located in the bifurcation. The long arrows signify the flow of blood into the aneurysm A where it impinges on the aneurysm wall thus exerting outward pressure causing the aneurysm to enlarge (small arrows).

FIG. 2a illustrates a side view of an implant 1 according to the invention in expanded state. Implant 1 is provided with a fixing section 3 and a distal section 5, with the distal section 5 being widened radially in comparison with the fixing section 3. It forms several loops that attach themselves to the wall of the aneurysm inside it.

Figure 1:
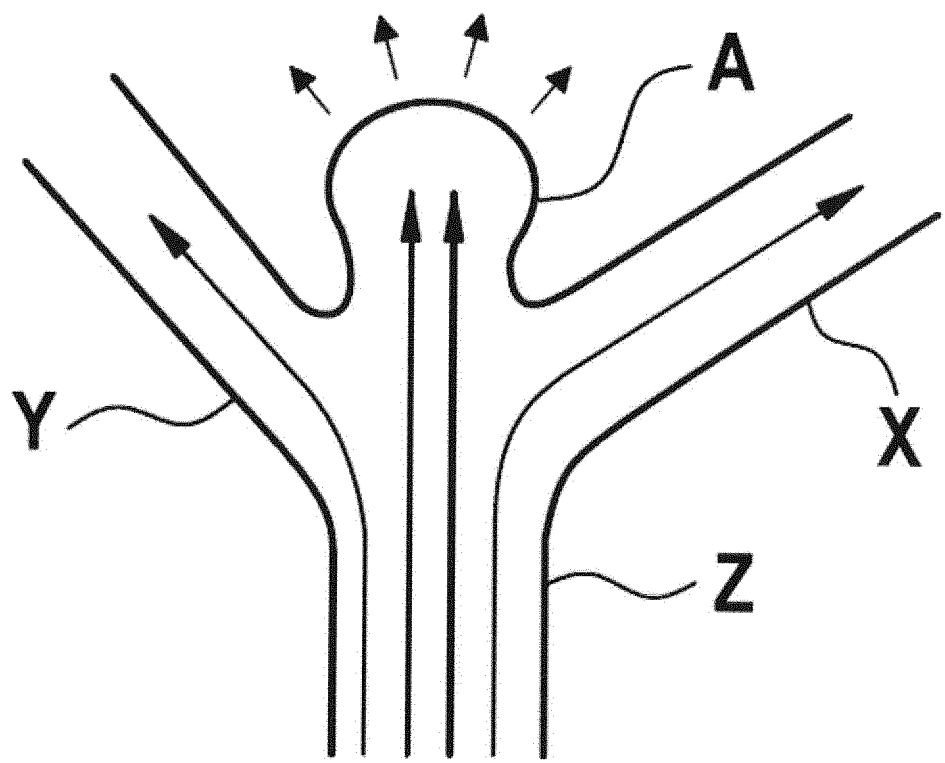
FIG. 1 shows a bifurcation aneurysm in schematic representation.

Between the fixing section 3 and the distal section 5 there is a transition section 4 that has a small cross-section. Seen from the proximal (in the drawing on the left) to the distal direction (in the drawing on the right), the webs arranged to form the implant 1 originating from fixing section 3 are closely brought together in the transition section 4 and then widen again to form the distal section 5. The webs/wires in the transition section may run at least to some extent through a sleeve 9 which holds the webs/wires together in the transition section. The fixing section 3 is connected via a 1st detachment point 6 with an introducer sheath 2, usually a guidewire. The transition section 4 has a 2nd detachment point 7. The distal section 5 is comprised of struts, loops and/or arches. The angle a the struts/loops/arches form in relation to the longitudinal axis L of the implant after placement ranges between −45° and +175°, wherein a positive angle α is indicative of struts/loops/arches pointing radially outward and a negative angle β of struts/loops/arches pointing radially inward. In the event of relatively regular bifurcation aneurysms the angle preferably is in the range of between +45° and +90°.

Figure 2A:
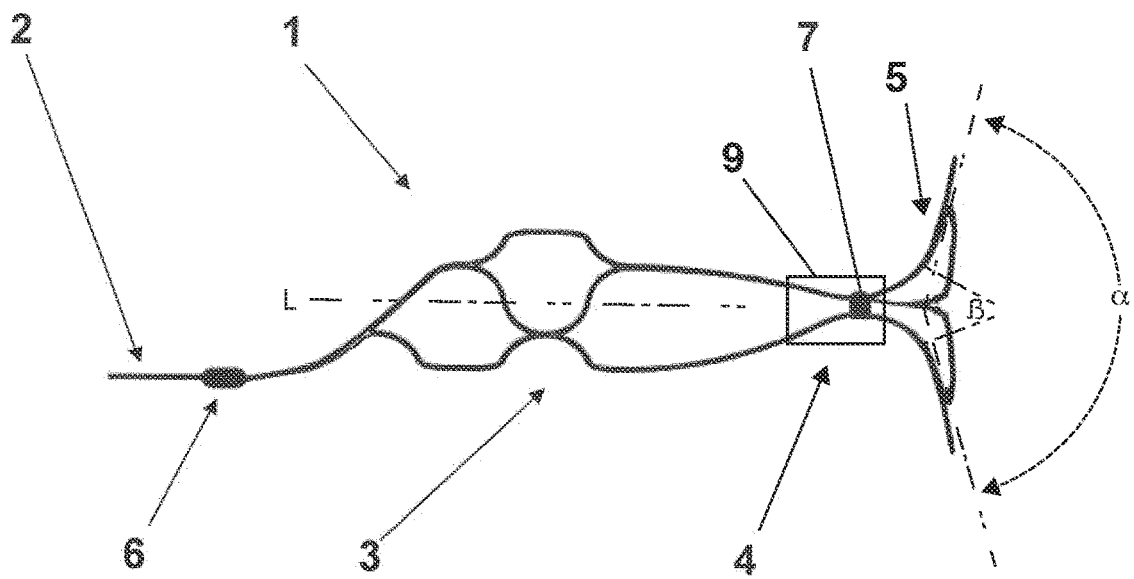
FIG. 2a illustrates an inventive implant with short fixing section seen from the side.
Figure 2B:
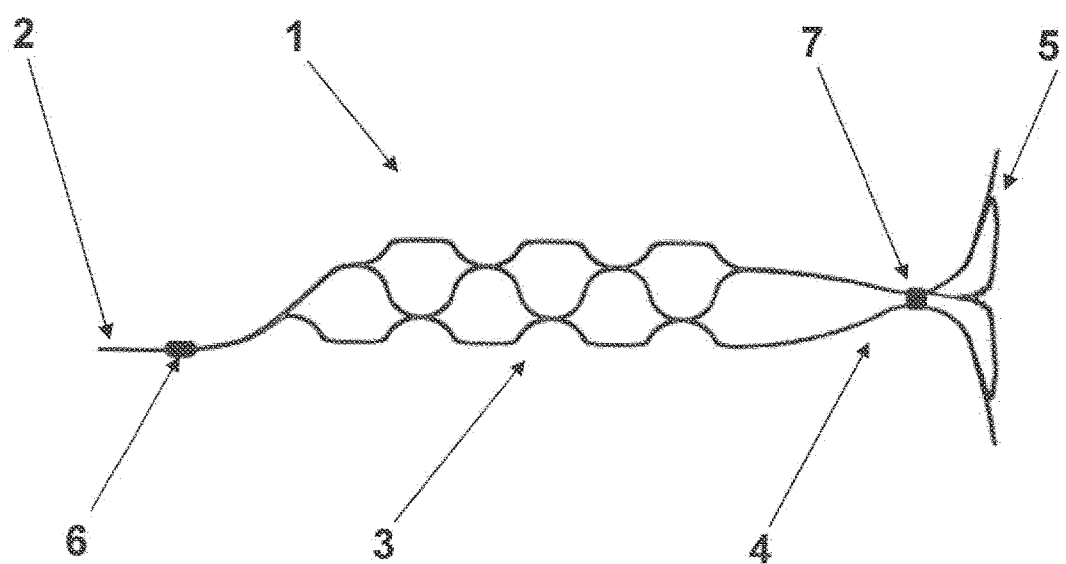
FIG. 2b illustrates an inventive implant with long fixing section seen from the side.

In FIG. 2b an implant 1 has been illustrated according to the invention, which largely corresponds to the one shown in FIG. 2a, but with a longer fixing section 3.

Figure 3A:
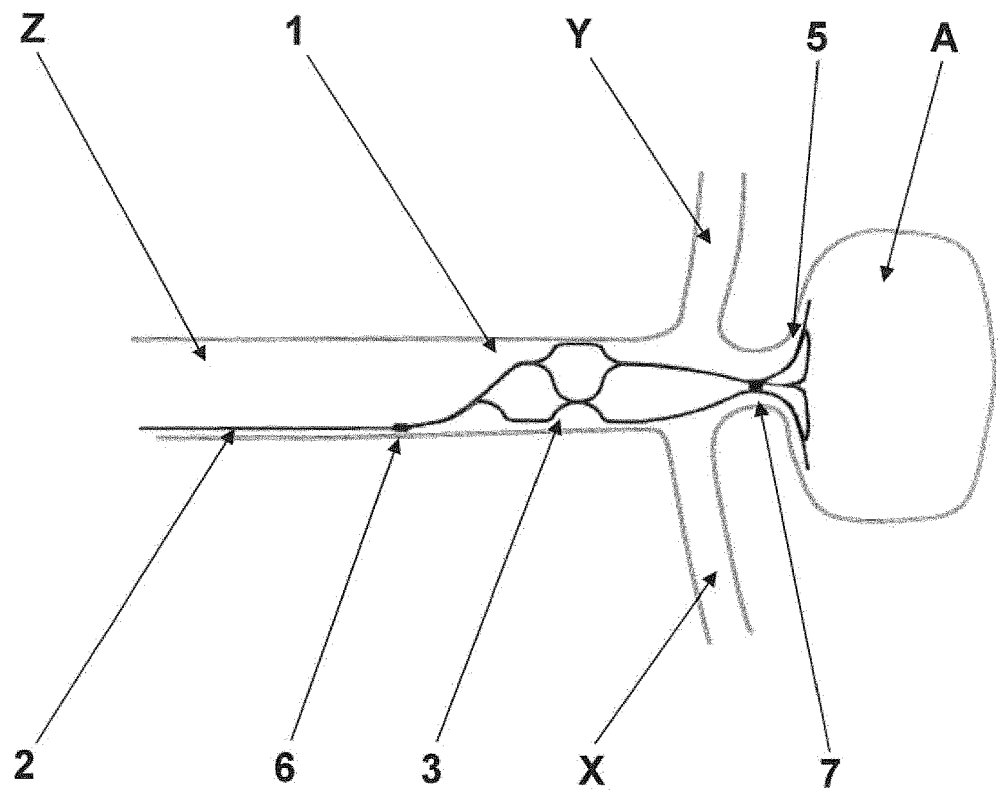
FIG. 3a shows an implant placed in position before detachment at the 1st detachment point.

FIG. 3a illustrates the placement of implant 1 shown in FIG. 2a in the region of a bifurcation aneurysm A. The aneurysm A is located in the area where the blood vessel Z branches off into the blood vessels X and Y. Implant 1 is placed such that the distal section 5 comes to rest in the entry area of aneurysm A, while the fixing section 3 makes sure the implant is safely secured in the blood vessel Z.

Figure 3B:
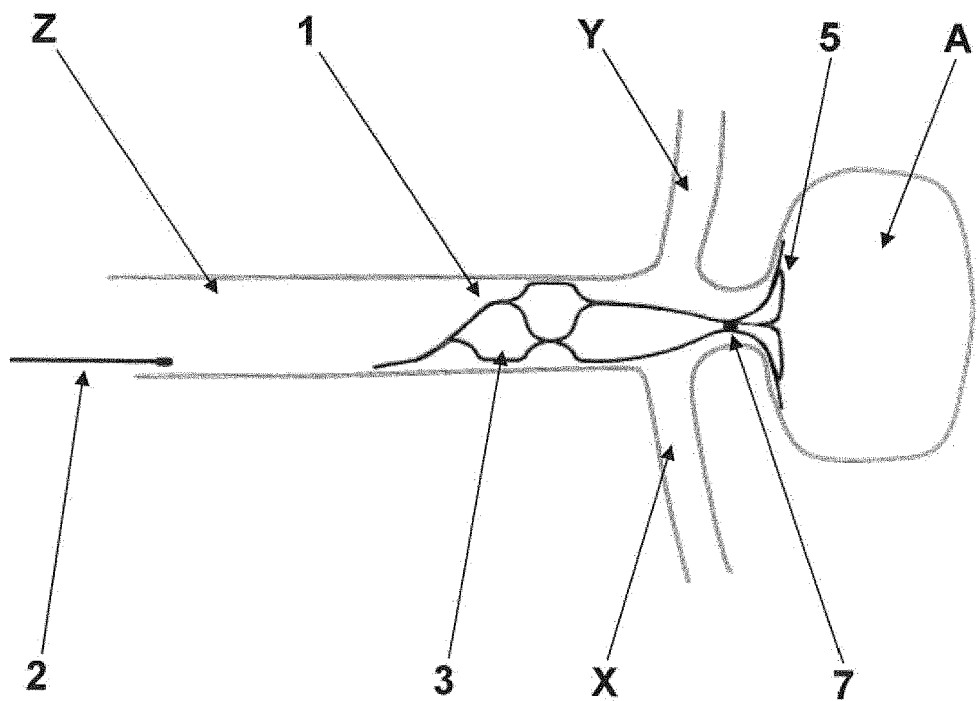
FIG. 3b shows the implant of FIG. 3a after detachment at the 1st detachment point.

FIG. 3b shows the corresponding situation after detachment of implant 1 at the first detachment point 6, i.e. in this case the distal section 5 remains in the blood vessel system together with the fixing section 3. The 2nd detachment point 7 remains intact.

Figure 4A:
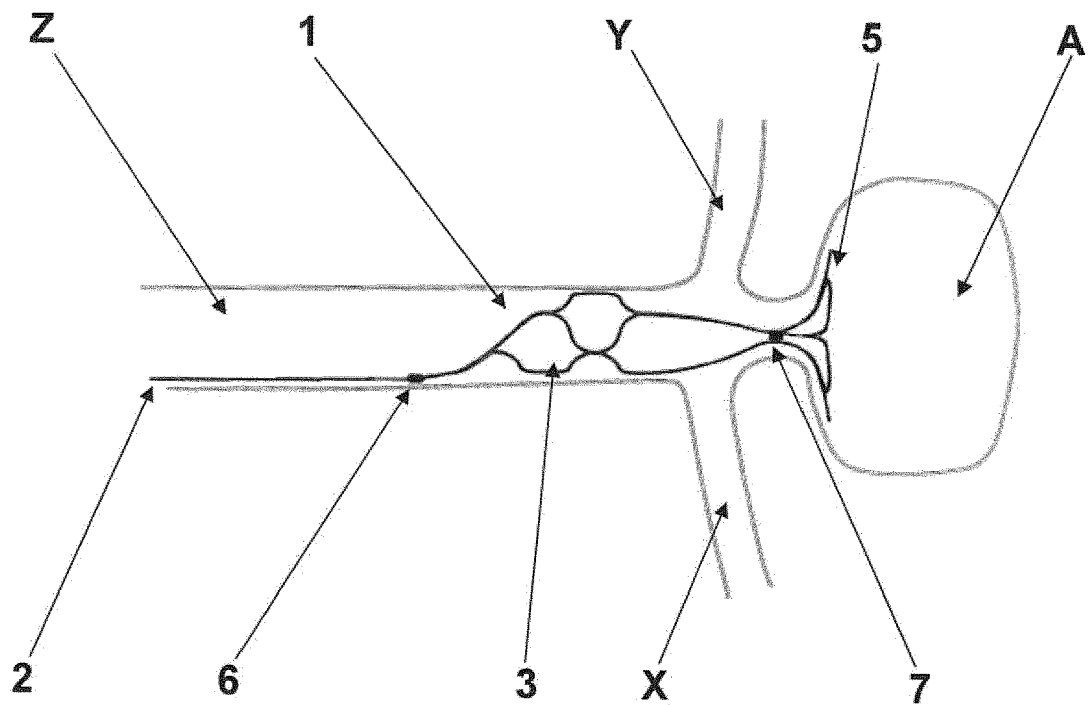
FIG. 4a shows an implant placed in position before detachment at the 2nd detachment point.
Figure 4B:
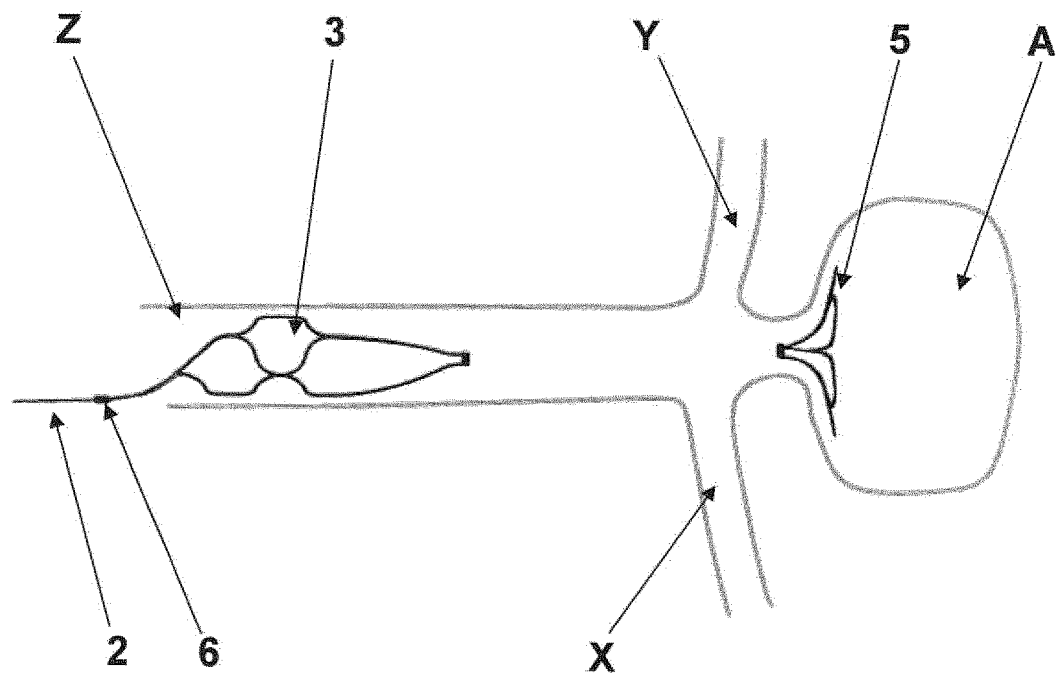
FIG. 4b shows the implant of FIG. 4a after detachment at the 2nd detachment point.

FIG. 4a shows a situation corresponding to the situation illustrated in FIG. 3a, where the attending physician decides, however, that the distal section 5 alone is sufficiently fixed in aneurysm A, that is, an additional fixation through fixing section 3 is not necessary. In this case, and as shown in FIG. 4b, the separation takes place at the 2nd detachment site 7. The insertion aid 2 is removed from the blood vessel system together with the fixing section 3; the 1st detachment point 6 remains intact.

Figure 5A:
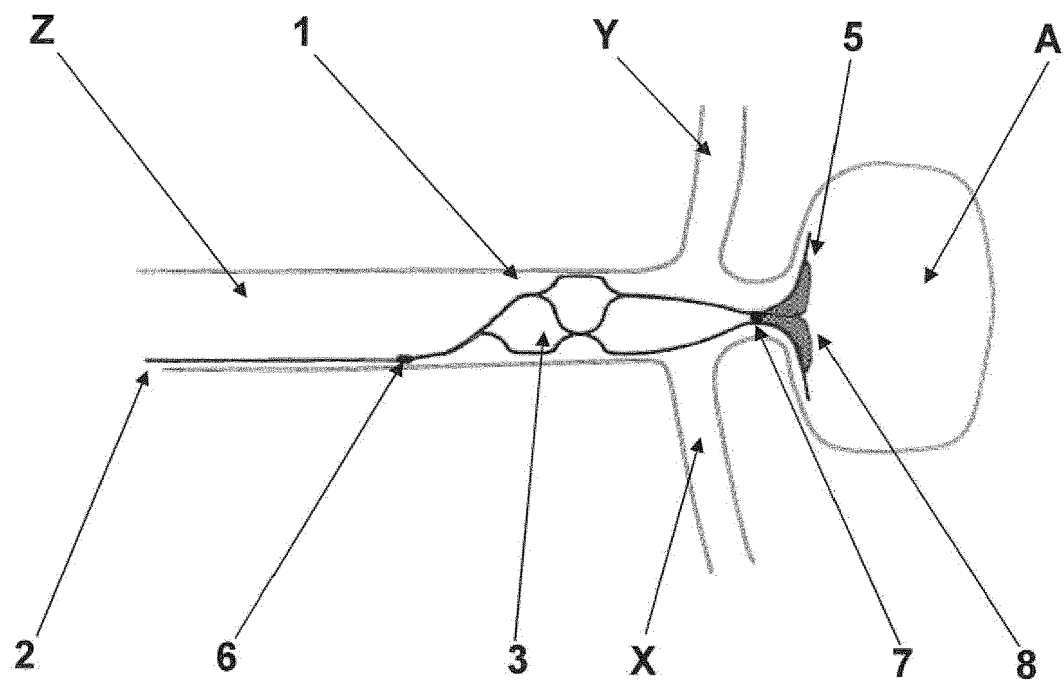
FIG. 5a shows an inserted implant with membrane before detachment at the 2nd detachment point.
Figure 5B:
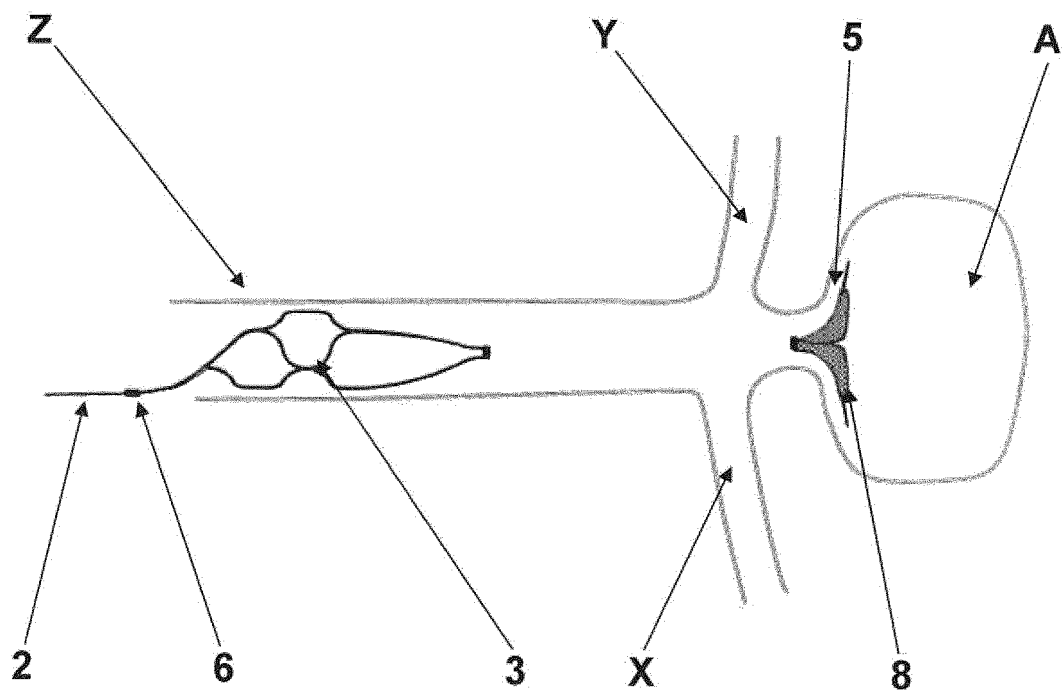
FIG. 5b shows the implant of FIG. 5a after detachment at the 2nd detachment point.

FIGS. 5a and 5b fully correspond to FIGS. 4a and 4b, but in this case the distal section 5 is covered with a membrane 8. This membrane additionally prevents blood from ingressing into the aneurysm A.

The invention claimed is:

1. An implant to be used for the occlusion of aneurysms (A) in blood vessels in the region of vascular branches, with the implant (1) being in an expanded state in which it is implantable in the blood vessel and in a contracted state in which it is movable through the blood vessel, with the implant (1) having a proximal fixing section (3) by means of which the implant (1) can be secured to the wall of a blood vessel, a distal section (5) where the implant (1) in the expanded state is radially widened relative to the proximal fixing section (3) and which is intended for placement in or in front of an aneurysm (A), and having a transition section (4) located between the proximal fixing section (3) and the distal section (5), wherein the proximal fixing section (3) is detachably connected to a delivery wire (2) via a 1st detachment point (6) characterized in that:
the transition section (4) is provided with a single 2nd detachment point (7) that enables the distal section (5) to be separated from the proximal fixing section (3);
the proximal fixing section (3) of the implant (1) is composed of interconnected or intersecting webs or wires; and
originating from the proximal fixing section (3) or distal section (5) the webs or wires run together and converge centrally in the transition section (4) and are fixed to the single 2nd detachment point (7).

2. An implant according to claim 1, characterized in that the 2nd detachment point is disposed along a central longitudinal axis (L) of the implant.

3. An implant according to claim 1, characterized in that all of the webs or wires in the transition section (4) extend at least to some extent through a single sleeve.

4. An implant according to claim 1, further comprising a first detachment mechanism for the 1st detachment point and a second detachment mechanism for the second detachment point, characterized in that the first detachment mechanism differs from the second detachment mechanism.

5. An implant according to claim 1, characterized in that the 2nd detachment point (7) is detachable electrolytically.

6. An implant according to claim 5, characterized in that the implant (1) is provided in whole or in part with an electrically insulating coating proximal to the 2nd detachment point (7).

7. An implant according to claim 1, characterized in that the distal section (5) comprises a plurality of struts, loops or arches that in the expanded state at least partially are facing radially outward.

8. An implant according to claim 7, characterized in that the struts, loops or arches in the expanded state form an angle ranging between ±45° and +175°, in relation to a longitudinal axis of the implant (1), wherein a positive angle stands for the struts, loops, or arches pointing radially outwards and a negative angle for the struts, loops, or arches pointing radially inwards.

9. An implant according to claim 7, characterized in that the loops or arches are provided inside with a membrane (8) or that a membrane (8) is spanned between the struts.

10. An implant according to claim 1, characterized in that the distal section (5) is radially widened in the expanded state so as to form a spherical, mushroom, anchor, or ellipsoidal shape.

11. An implant according to claim 1, characterized in that one or several separation elements are arranged centrally in the distal section (5), said one or several separation elements at least partially occluding the neck of the aneurysm (A) in the implanted state.

12. An implant according to claim 11, characterized in that the one or several separation elements are formed from fibers, threads, wires or membranes (8).

13. An implant according to claim 11, wherein the one or several separation elements are formed from membranes (8), characterized in that each membrane (8) in an expanded state extends in a proximal direction and has a conical or pyramid form.

14. An implant according to claim 12, wherein the one or several separation elements are formed from membranes (8), characterized in that each membrane (8) has one or several openings or in that in each membrane (8) one or several openings can be produced by a piercing method.

\* \* \* \* \*